US00PP13754P39

(12) United States Plant Patent
van Schie

(10) Patent No.: US PP13,754 P3
(45) Date of Patent: Apr. 29, 2003

(54) GUZMANIA PLANT NAMED 'DEPLAKAR'

(76) Inventor: Hubertus L. van Schie, Delftsestraatweg 15B, 2645CA, Delfgauw (NL)

( * ) Notice: Subject to any disclaimer, the term of this patent is extended or adjusted under 35 U.S.C. 154(b) by 0 days.

(21) Appl. No.: 10/095,443

(22) Filed: Mar. 13, 2002

(65) Prior Publication Data

US 2003/0046745 P1 Mar. 6, 2003

(30) Foreign Application Priority Data

Aug. 28, 2001 (EP) ..... 2001/1359

(51) Int. Cl.[7] ..... A01H 5/00

(52) U.S. Cl. ..... Plt./371

(58) Field of Search ..... Plt./371

*Primary Examiner*—Kent Bell

(74) *Attorney, Agent, or Firm*—Foley & Lardner

(57) ABSTRACT

A new and distinct Guzmania plant named 'Deplakar' characterized by compact plant shape; short leaves; compact inflorescence shape; yellow-orange floral bracts with red to orange-red tips.

2 Drawing Sheets

Latin name of the genus and species of the plant claimed: *Guzmania hybrid.*
Variety denomination: 'Deplakar'.

BACKGROUND OF THE INVENTION

The present invention comprises a new and distinct cultivar of Guzmania plant, hereinafter referred to by the cultivar name 'Deplakar'. The genus Guzmania is a member of the family Bromeliaceae.

Guzmania comprise a genus of over 100 species of herbaceous evergreen perennials suitable for cultivation in the home or under glass. Guzmania are predominantly epiphytic with a few terrestrial species and are native to the tropics. For the most part the species vary in diameter from 7 or 8 inches to 3 or 4 feet and have rosettes of glossy, smooth edged leaves.

Floral bracts of Guzmania frequently have brilliant colors and may last for many months. The range of flower colors for Guzmania is generally from the yellow through orange but may also include flame red and red-purple. White or yellow, tubular, three petalled flowers may also appear on a stem or within the leaf rosette but are usually short lived.

Guzmania may be advantageously grown as potted plants for greenhouse or home use. Desirably the plants are shaded from direct sunlight during the spring to autumn period, the central vase-like part of the leaf rosette is normally filled with water.

Guzmania is native to tropical America. Leaves of the Guzmania are usually formed as basal rosettes which are stiff and entire and in several vertical ranks. Guzmania have terminal spikes or panicles which are often bracted with petals united in a tube about as long as the calyx.

Asexual propagation of Guzmania is frequently done through the use of tissue culture practices. Propagation can also be from off-shoots which are detached from the mother plant, and may be grown in an appropriate soil or bark mixture.

The new cultivar 'Deplakar' is a naturally occurring branch mutation of Guzmania 'Marjan' (unpatented), and originated by the inventor Hubertus L. van Schie, in 1998 in Delfgauw, The Netherlands. The selection comprising the new variety was chosen after commencement of flowering in 1998.

The new cultivar was asexually propagated by taking cuttings by Deroose Plants in Evergem, Belgium in 1998. Asexual propagation by tissue culture was initiated in 1999. Continuous asexual propagation has demonstrated that the combination of characteristics as herein disclosed for the new cultivar 'Deplakar' are firmly fixed and are retained through successive generations of asexual reproduction. The new cultivar reproduces true to type.

BRIEF SUMMARY OF THE INVENTION

The following traits have been repeatedly observed and are determined to be basic characteristics of 'Deplakar' which in combination distinguish this Guzmania as a new and distinct cultivar:

1. Compact plant shape;
2. Short leaves;
3. Compact flower shape;
4. Yellow-orange floral bracts with red to orange-red tips; and
5. Green leaves.

'Deplakar' has not been observed under all possible environmental conditions. The phenotype of the new cultivar may vary significantly with variations in environment such as temperature, light intensity, and daylength without any change in genotype.

Of the many conmmercial cultivars known to the present inventor, the most similar in comparison to 'Deplakar' is the parental cultivar 'Marjan' which is characterized by its yellow inflorescence with red/orange tips. In comparison to 'Marjan', the inflorescences, leaves, and plant shape of 'Deplakar' are more compact. The leaf length of 'Deplakar' is shorter than the leaf length of 'Marjan', when grown under similar conditions. The length of the inflorescence of 'Deplakar' is shorter than the inflorescence length of 'Marjan'.

BRIEF DESCRIPTION OF THE DRAWING

The accompanying photographic illustrations shows a 19-month-old 'Deplakar' plant propagated by tissue culture following growth under appropriate growing conditions, with colors being as true as possible with illustrations of this type.

The drawing at the top of sheet one depicts a close-up view of the inflorescence and foliage characteristics of 'Deplakar'.

The drawing at the bottom of sheet one depicts a side view of a typical plant of 'Deplakar'.

The drawing on sheet two depicts 'Deplakar' on the right and 'Marjan' on the left.

DETAILED BOTANICAL DESCRIPTION

The following observations, measurements and values describe 19 month old plants grown in 14 cm pots in Delfgauw, The Netherlands under greenhouse conditions which closely approximate those generally used in horticultural practice. 'Deplakar' is grown in a commercial greenhouse under 21 degrees Celsius day and night. No artificial lighting or photoperiodic treatments are conducted but 'Deplakar' is forced into flowering by adding acetylene. Highest temperature resistance is 40 degrees Celsius, the lowest 5 degrees Celsius. Direct sunlight has to be avoided because it causes burning of the leaves. The following fertilizer is added: 1 part nitrogen, 0.5 parts phosphorus 3 parts Kalium and 0.2 parts Magnesium. Water should not contain too much salts. From the start of tissue culture it takes five years to produce a commercial plant. The amount of time needed to produce an inflorescence depends on the amount of acetylene added. The inflorescences have a tenability of up to six months depending on the environment they are grown and kept in.

Color references are made to The Royal Horticultural Society Colour Chart (R.H.S.), except where general colors of ordinary significance are used.

Parentage: Parent: Guzmania 'Marjan'.

Propagation: By tissue culture.

Plant:

*Form.*—Upright, leaves in basal rosette.

*Height.*—Average 35 cm.

*Diameter.*—Average 60 cm.

*Growth habit.*—Upright, growth moderate.

Foliage:

*Size.*—Leaves have an average length of 39 cm and an average width of 3.5 cm (measured at the middle of a leaf). Leaves are variable in width (even on one plant); width of mature leaf varies from 2.3 cm to 4.3 cm.

*Shape.*—Linear to narrow linear, tips acuminate to long acute.

*Margin.*—Entire.

*Surface texture.*—Smooth, glossy.

*Leaf color.*—Upper side yellow-green, closest to but greener than RHS 146A; under side yellow-green, RHS 146A.

Bracts:

*General shape/arrangement.*—Broad lanceolate, arranged alternately, tips bent downwards in an average angle of 40° to 85° (0°= horizontal).

*Scape bracts.*—Length: Average 21.5 cm. Width: Average 4.1 cm. Margin: Entire. Apex: Apiculate. Color: Upper side orange-red, RHS 34A to 34B; upper half of upper side yellow-green, RHS 147A; under side orange-red RHS 34A; upper half of under side yellow-green, RHS 146A. Number: Average 9.

*Primary bracts.*—Length: Average 17.8 cm. Width: Average 3.8 cm. Margin: Entire. Apex: Apiculate. Color: Upper side orange-red, RHS 33B to 34B; tips very dark yellow-green, darker than but closest to RHS 147A to dark gray-purple, darker than but closest to RHS N186A; under side orange-red RHS 3A to 3B; tips yellow-green, RHS 147A. Number: Average 9.

*Floral bracts.*—Length: Average 12 cm. Width: Average 2.6 cm. Margin: Entire. Apex: Apiculate. Color: Upper side yellow-orange, RHS 21A to 23A; tips red to orange-red, RHS 46B to RHS N34A; under side yellow-orange to orange-red, RHS 20A to 31A, tips orange-red, RHS N34A. Number: Average 9.

Inflorescence:

*Borne.*—Each inflorescence consists of an average of 9 individual flowers, inflorescences placed vertically, tops approximately 7 cm from top of bract, only very few inflorescences appear; average length of inflorescence 5 cm.

*Individual flowers.*—Average length 2.5 cm; average width 0.4 cm.

*Sepals.*—The perianth consists of one large sepal, narrow and oblong, slightly folded, average length 6.3 cm, average width 9 mm; outer color yellow-green, RHS 151A, tip yellow-orange RHS 17A, lighter color at the base, RHS 153D; inner color yellow-green, RHS 151A, yellow-orange tip, RHS 17A, lighter at the base, RHS 153D.

*Petals.*—6 petals, linear. Outer petals: 3 outer petals, average length 3.2 cm, average width 4 mm, green-white color, RHS 157A on both sides, yellow tips, RHS 6D; Inner petals: 3 inner petals, average length 2.6 cm, average width 4 cm, yellow-orange color, RHS 17A on both sides, lighter base, yellow RHS 12B to 12C.

*Calyx.*—Average length 2.5 cm; average width 9 mm, white, RHS 155D.

*Corolla.*—Average length 1 cm, yellow, RHS 12A.

*Time of blooming.*—Summer.

*Duration of inflorescence.*—More than one month.

Reproductive organs:

*Ovary.*—Ovate, average length 5 mm; average width 3 mm; light yellow-green in color, RHS 150D to green-white, RHS 157A. Ovary ribbed axially, due to three locules.

*Style.*—Average length 1.5 cm; yellow in color, RHS 7 B, stigma cleft in two parts, approximately 2 mm long; yellow RHS 7 A to 7 B.

*Stamens.*—Average 6, basifixed, shaped narrow sagittate, average length 6 mm; average width 1 mm; green-white in color, RHS 157A. Anthers: Yellow, RHS 4D. Pollen: Very little, light yellow color, closest to RHS 4C to 4D.

Roots: Thin, very well-branched, strong to moderately strong; color greyed-orange, RHS 165A.

Seed characteristics: No fruits or seeds observed to date.

Pest/disease resistance/susceptibity: No observations to date.

I claim:

1. A new and distinct Guzmania plant named 'Deplakar' as described and illustrated herein.

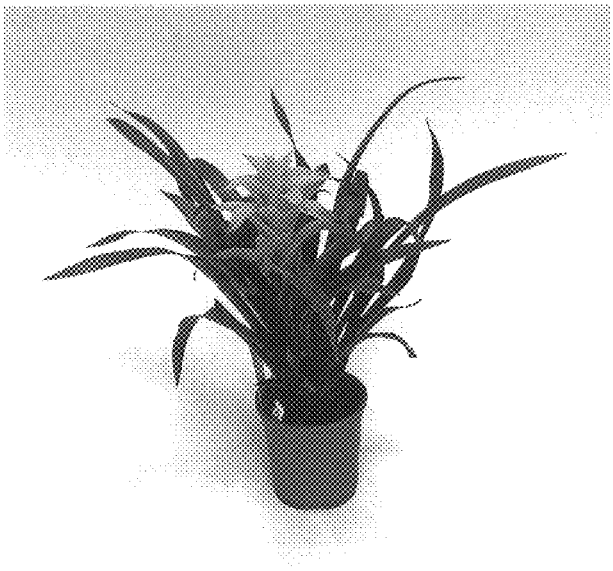
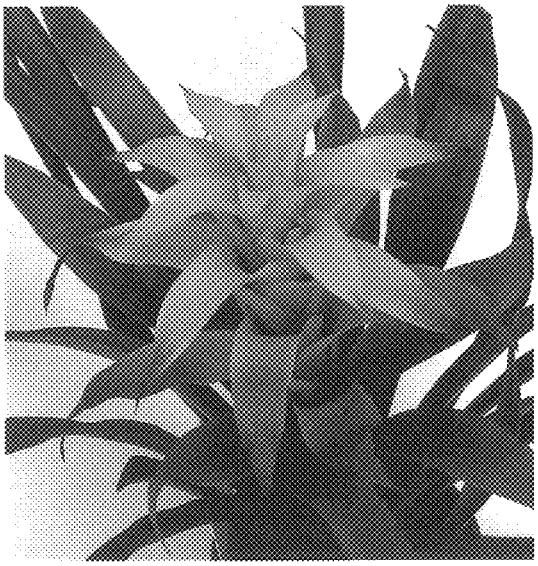

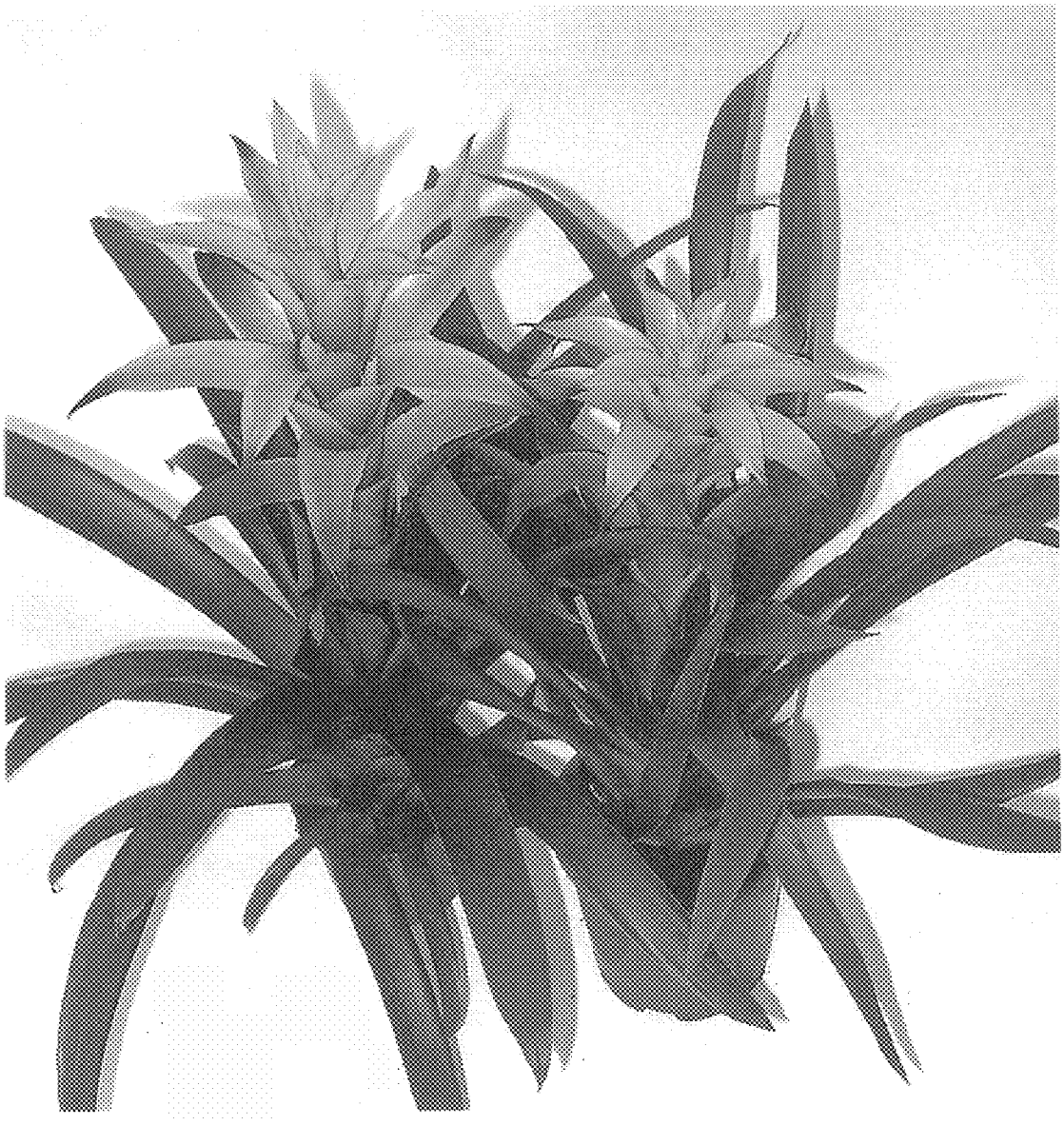

* * * * *